United States Patent [19]

Vacquer

[11] Patent Number: 5,377,551
[45] Date of Patent: Jan. 3, 1995

[54] PROBE FOR PENETRATING AND DISPLACING PARTICULARLY INTO A MASS OF PULVERULENT MATERIAL

[75] Inventor: Benoit Vacquer, Rouen, France

[73] Assignee: Desinsectisation Moderne, Rouen, France

[21] Appl. No.: 720,838

[22] Filed: Jul. 15, 1991

[30] Foreign Application Priority Data

| Mar. 2, 1990 [FR] | France | 90 02684 |
| Mar. 2, 1990 [FR] | France | 90 02685 |

[51] Int. Cl.⁶ .............. B25D 9/06; E21B 7/26; E21C 3/24; G01N 33/02
[52] U.S. Cl. .............. 73/864.45; 73/84; 73/864.64; 173/91; 175/19; 175/20; 175/21
[58] Field of Search ............ 73/84, 864.45, 864.64; 175/19–21; 173/91, 92; 405/232, 259.6

[56] References Cited

U.S. PATENT DOCUMENTS

| 2,542,086 | 3/1983 | Maitre . | |
| 3,091,968 | 6/1963 | Platzer | 73/864.64 |
| 3,106,148 | 10/1963 | Bothe et al. . | |
| 3,554,303 | 8/1968 | Zajkowski . | |
| 3,763,939 | 10/1973 | Sudnishnikov et al. . | |
| 3,942,595 | 3/1976 | Sudnishnikov et al. . | |
| 3,955,631 | 5/1976 | Kostylev et al. . | |
| 4,070,948 | 1/1978 | Tkach et al. | 175/19 |
| 4,179,930 | 12/1979 | Chrisp . | |
| 4,398,414 | 8/1983 | MacGregor | 73/84 |
| 4,537,265 | 8/1985 | Cox et al. | 173/91 |
| 4,632,191 | 12/1986 | McDonald et al. | 173/91 |
| 4,646,277 | 2/1987 | Bridges et al. . | |
| 4,749,050 | 6/1988 | Ritter . | |
| 4,770,030 | 9/1988 | Smith | 73/84 |
| 4,800,765 | 1/1989 | Nelson | 73/864.64 |
| 4,806,153 | 2/1989 | Sakai et al. . | |
| 4,809,789 | 3/1989 | MacFarlane | 173/91 |
| 4,858,703 | 8/1989 | Kinnan . | |
| 4,858,704 | 8/1989 | McDonald et al. | 175/19 |
| 4,866,997 | 9/1989 | Kaufman . | |
| 5,031,706 | 7/1991 | Spektor | 173/92 |
| 5,062,486 | 11/1991 | McClenahan | 173/91 |

FOREIGN PATENT DOCUMENTS

| 2542086 | 9/1984 | European Pat. Off. . |
| 0262882 | 4/1988 | European Pat. Off. . |
| 0263281 | 4/1988 | European Pat. Off. . |
| 5470970 | 11/1977 | Japan . |

*Primary Examiner*—Hezron E. Williams
*Assistant Examiner*—George M. Dombroske
*Attorney, Agent, or Firm*—Schweitzer Cornman & Gross

[57] ABSTRACT

The invention relates to a probe assembly (1) adapted to penetrate and travel in a mass of material, comprising:
a hull,
a front striking zone (3) and/or a rear striking zone (4) axially opposite, for transmitting pulses to the hull,
a striking piston (2) and
a pneumatic motor for setting in motion the striking piston (2) so as to project it against a striking zone (3, 4) integral with the hull, a compressed-air supply for the motor, characterized by the fact that the friction of the hull and any guiding elements rigidly connected to the hull in a pulverulent mass is between a lower value f insufficient to assure the holding of the probe upon the recoil of the striking piston (2) and a higher value F preventing the probe from advancing upon the impact of the striking piston (2) on the striking zone (3, 4) so as to permit the advancement of the probe in the pulverulent material.

7 Claims, 6 Drawing Sheets

PROBE FOR PENETRATING AND DISPLACING PARTICULARLY INTO A MASS OF PULVERULENT MATERIAL

BACKGROUND OF THE INVENTION

The invention relates chiefly to a device, for example, to one of the probe type, for penetrating and advancing into a mass of pulverulent or heavy material, typically grains, seeds or sand.

The device of the present invention can penetrate into and travel in the mass of pulverulent material, that is, for example, in a pile, a geological formation, a ship's hold or a silo or any other storage unit.

It is known on the one hand to produce a percussion apparatus for penetrating into the interior of a solid, for example, percussion drills that make it possible to drill a hole into concrete, or the earth torpedoes, which are described in French Patent 72 51742 published under number 2 161732, which enable holes to be bored in the soil.

The use of percussion devices for penetrating or advancing in pulverulent materials has never been envisaged. Furthermore, devices of the known type do not permit such use to the extent that, in a pulverulent material such as grain, the resistance to advancement comes chiefly from friction on the sides of the device. In solids, however, the resistance to advancement comes mainly from the difficulty in making a hole. The presence of the hole diminishes the pressure exerted on the sides of the apparatus. Therefore, in the experiments performed in the development of the invention, apparatuses of the known type, which concentrate 80% of their energy at the head, ceased to advance into the interior of a mass of grain at the end of a few meters. The body of the earth torpedo was immobile while the head was vibrating without producing any progress. Moreover, the applicant Company has discovered that probes having too little friction in proportion to the pulverulent material, do not succeed in advancing. The value $f_i$ of the friction of the hull of the probe, and of any guiding means rigidly attached to the hull, must be greater than the minimum value f at which the recoil of the striking piston produces a recoil of the probe. Of course, the value $f_i$ of the friction must be less than the maximum F at which the impact of the striking piston on the striking zone no longer causes the probe to advance. The user determines the optimum value of the friction taking into account the mass and the natural frequency of the probe, as well as the amount of motion delivered by the driving means to the striking piston. Tests permit optimizing the friction value, doing so for various loads pulled or pushed. The value $f_i$ can be modified, particularly increased, by the addition of guiding means fixedly attached to the hull of the probe. The value $f_i$ of the friction is substantially proportional to the surface area the probe and the added guiding means. So, to increase the value of $f_i$, it is also possible to add a long guiding tube of small diameter or a shorter guiding tube of greater diameter. The choice of the guiding elements to be added is determined by the geometry of the container of the pulverulent material to be explored, or by the treatments to be performed within the said pulverulent material.

There exists no known method for penetrating into the interior of a pulverulent mass of ore, sand or grains.

The case of grain is particularly important. To inspect or effectively and lastingly protect cereal grains against pests it is necessary to be able to penetrate into the mass. The protection of the world's cereal reserves is one of the major economic objectives of our time. Destroying pests makes it possible to feed people.

SUMMARY OF THE INVENTION

The device according to the present invention permits penetrating and advancing inside of a pulverulent mass to perform the necessary observations, take samples, or perform a desired treatment. To penetrate and advance in the mass, the device according to the present invention comprises a striking piston intended to apply impacts to at least one striking zone. Since the striking zone is connected, preferably rigidly, to the structure of the device according to the present invention, the impact of the striking piston on the striking zone produces the advancement of the probe.

In one embodiment, the probe according to the present invention is of an ogival shape.

The striking piston is set in motion by the action of motor means. In a first variant of embodiment of the probe according to the present invention, the motor means are electromagnetic, for example of the linear motor type. In one advantageous variant of the probe according to the present invention, the striking piston is driven by a fluid. In a particularly advantageous variant of the probe of the present invention, the fluid is compressed air.

The use of fluids to drive the striking piston avoids the generation of sparks, which are very dangerous, for example, in a grain elevator whose atmosphere may be explosive.

The use of compressed air as driving fluid for the striking piston makes it no longer imperative to prevent any leakage of the said fluid. On the contrary, it may prove advantageous to produce the escape of the air within the pulverulent mass being penetrated. Thus, on the one hand there is no need to arrange for an exhaust tube, and on the other hand a fluidization of the pulverulent mass is provided, which facilitates the advance of the probe according to the present invention.

This fluidization is particularly efficacious, in the case of grain, if the exhaust is performed on the sides of the probe. Moreover, exhausting the air inside of the pulverulent mass permits using it to carry treatment products. The air can serve, for example, as a vehicle for products intended to eliminate parasites from within a mass of grain. For example, methyl bromide of the formula $CH_3Br$ can be injected.

Advantageously, the probe according to the present invention comprises a rear striking zone and means to permit the striking piston to strike only or mainly on this rear striking zone. This permits the probe to be driven in reverse in order, for example, to maneuver it for its retrieval.

Advantageously, the probe according to the present invention comprises remote control means to shift either forward or backward.

Depending on the medium to be treated, an electromagnetic wave remote control will be used, such as radio waves, or a control by fluids. The electromagnetic control signal is received by a remote control receiver module of a known type. Remote control by fluid is performed advantageously by a rotary jack as described further on.

In one advantageous embodiment, the remote control of the direction is performed by rotation of a cable, e.g., a steel cable.

Advantageously, in the absence of remote control signals, the apparatus is automatically put into backward. Thus, in case of breakdown of the remote control device it will always be possible to recover the probe, for example by sending it only the motor energy. A rearward movement command is obtained in the absence of the remote control signals by using, for example, a return spring providing the shift to backward movement, the force of the spring having to be overcome in order to shift to forward movement or, in the example of a rotary jack, the switching surface area for shifting to reverse is definitely greater than what is necessary for shifting to forward movement.

In the case of pneumatic remote control, either a tube for controlling forward movement, a tube for controlling backward movement, in addition to a tube for supplying the striking piston, or else a single tube for controlling forward movement, involving a pressure greater than the feed pressure of the striking piston, the tube for feeding the striking piston providing a feed for the control, for example, of the backward movement.

Advantageously, the tube for feeding fluid and/or the electric power is of as small a diameter as possible to minimize friction. Advantageously, umbilical tubes are used having clustered tubes needed for supplying energy and for carrying remote control data and/or containing cables transmitting the remote control signals by their rotation.

The probe according to the present invention can be equipped with data acquisition means.

To permit a visual inspection of the pulverulent material use is made either of endoscopes, particularly optical fiber endoscopes, or television cameras, operating for example in the visible or infrared spectrum.

Electroacoustical transducers, e.g., piezoelectric transducers, permit the performance of echography.

Receptacles that can be opened by remote control permit the taking of samples of the pulverulent material.

Thermometers, e.g., thermocouple thermometers, permit the measurement of temperature.

Manometers permit measurement of the pressure exerted by the pulverulent material and/or by the gases which it contains.

Electrodes permitting measurement of the electrical resistivity of the pulverulent material.

Emitters of electromagnetic waves such as gamma rays, X-rays, microwaves and/or radio waves enable the measurement of the nature or state of the pulverulent material. The same applies to emitters and/or receivers of particles such as alpha or beta radiation.

In one variant embodiment, the probe comprises only an emitter or only the receiver, the complementary receiver or emitter being situated either outside of the mass of pulverulent material, or on one or more probes, for example, following parallel paths.

The wavelength of the energy emitted is adapted to the nature of the material that will be encountered and/or to the characteristics which are to be measured or determined. The same applies to processing performed on the signals received, such as Doppler processing or the elimination of standing waves.

Advantageously, in a first variant embodiment, the probe according to the present invention has at the front a tube of great length and small diameter rigidly affixed to the hull. For example, the said tube is 2 meters long and 2 centimeters in diameter.

In a second variant embodiment, the probe according to the present invention has at the front a tube of large diameter, such as one near to or slightly larger than the diameter of the hull. This tube is affixed rigidly to the hull. In a variant embodiment, this tube is 2 meters long and 80 millimeters in diameter, the hull having a length of one meter and a diameter of 70 millimeters with an extra thickness at the level of a lateral exhaust where the diameter of the probe is equal to 80 min. Such a tube shall be called a "guide tube" in the remainder of the disclosure, to the extent to which it improves the straight-line penetration of the probe. Moreover, the guide tube facilitates the retrieval of the probe.

The guide tube provides for obtaining the desired friction value in the pulverulent mass in order to optimize the advancement of the probe. It is well understood that a guide tube can contain products or equipment to be deposited within the mass of the pulverulent products.

In the case of vertical penetration into grain, a probe according to the present invention, having no guide tube, when running backward stops in the best of cases at two meters from the surface, often at 4 to 6 meters. The probe no longer finds the support to be able to recoil. The guide tube which in this case constitutes a rigid pole driven into the grain permits the probe to be drawn back to the surface by the sole use of percussion.

Advantageously, the front end of the probe or guiding tube is equipped with cushioning means, consisting for example of a block of rubber. The cushioning means prevents damage to the container of the pulverulent material, such as for example the bottom of the hold of a ship or the bottom of a silo.

Advantageously, the sample taking means are situated near the front end of the guide tube. Thus the taking of samples is performed two meters ahead of the body of the probe. This space of two meters is particularly important in cases where, due to the driving power and the nature of the material to be penetrated, the depth of penetration of the probe is limited.

Advantageously, the probe according to the present invention, or the guide tube if any, is provided with means for depositing solid materials in the mass of pulverulent material. For example, a cap is affixed to the body to be deposited and is hooked to the probe, or advantageously to the front end of the guide tube.

In a variant embodiment, the material to be deposited is hooked to a ring held by abutments, advantageously offset (which permits increasing the diameter of the ring in relation to the diameter of the guide tube). When the reversal of the probe according to the present invention takes place, the ring or the cap as well as the materials hooked thereto are abandoned.

Advantageously, the probe according to the present invention comprises guiding means. For example, the guiding means consists of excrescences which can be deployed on the periphery of the hull of the probe. Deploying an excrescence breaks the symmetry of the probe and prevents straight-line movement. The deployment of the excrescences is advantageously programmed or remotely controlled.

Advantageously, the probe according to the present invention has means provided for indicating its position.

The data acquisition means are coupled with means for recording the data gathered by the data acquisition means and/or transmitted to operators or to recording means situated on the surface.

Advantageously, the probe according to the present invention includes hitching means advantageously placed at the front or rear for laying tubes within the mass of the pulverulent material. Advantageously, the position of the tube will not interfere with the withdrawal of the probe in reverse. In a variant embodiment, the probe passes, for example, through a pile of pulverulent material towing behind it a tube which comes out through the other side.

The invention has principally as its subject matter a probe adapted to penetrate and advance in a mass of material, which has:
  a hull,
  a front striking zone and/or a rear striking zone, axially opposed, for transmitting impulses to the said hull,
  a striking piston, and
  motor means for moving the said striking piston so as to project it against a striking zone integral with the hull, compressed-air feeding means supplying the motor means, characterized by the fact that the friction of the hull and any guiding elements rigidly tied to the said hull in a pulverulent material is between a lower value f insufficient to hold the probe upon the recoil of the striking piston, and an upper value F preventing the advancement of the probe upon the impact of the striking piston on the striking zone so as to permit the advancement of the probe in the pulverulent material, particularly agricultural products.

The invention also has as its subject a method for treating an organic, pulverulent mass, particularly agricultural products or grains, characterized by the fact that it comprises a step consisting of causing a percussion probe to penetrate into the mass.

DESCRIPTION OF THE DRAWINGS

The invention will be better understood from the following description of drawings given as non-limiting examples, among which:

In FIGS. 1 to 9 the same reference numbers have been used to identify the same elements.

DETAILED DESCRIPTION OF THE INVENTION

Figure 1:
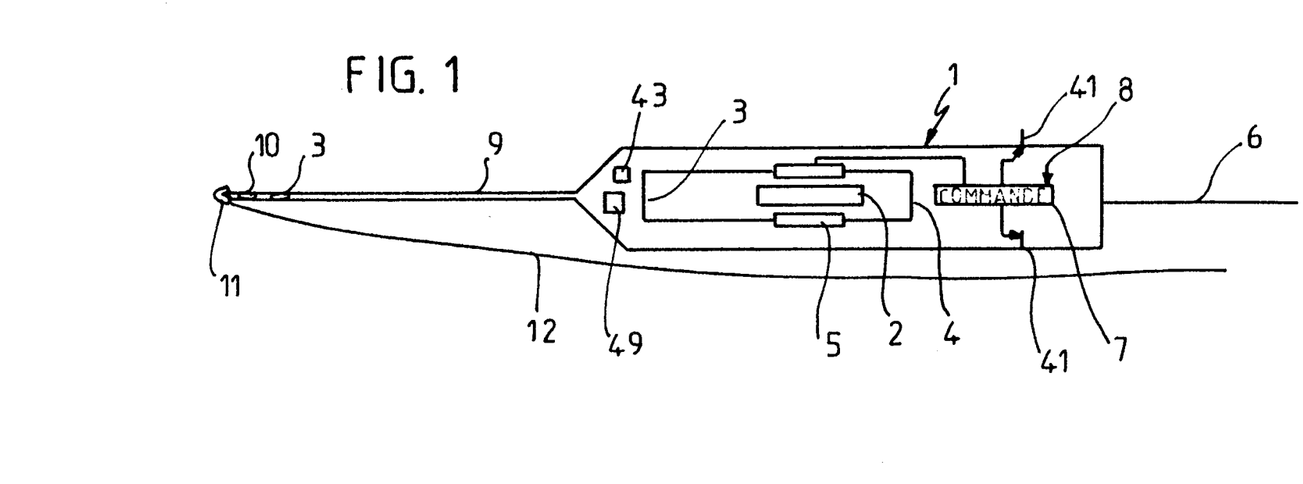
FIG. 1 is a sketch explaining the principle of operation of the probe according to the present invention.

In FIG. 1 can be seen an embodiment of probes according to the present invention. The probe 1 comprises a hull in which there is created a hollow containing a striking piston. The hollow comprises a striking zone 3. The repeated impacts of the striking piston 2 on the striking zone 3 enable the advance of the probe 1. Advantageously, the hollow provided in the hull of the probe 1 has a striking zone 4 axially opposite the striking zone 3. The impact of the striking piston 2 on the striking zone 4 causes the probe 1 to retract. The probe 1 comprises motor means 5 intended for the driving of the striking piston 2. The motor means 5 communicate a movement to the striking piston 2 toward the striking zone 3 or the striking zone 4.

At the moment of the impact of the striking piston 2 on the striking zone 3 or 4, the kinetic energy of the striking piston is to a great extent transmitted to the hull of the probe 1, which thus advances or moves back according to the direction of operation.

Various types of motor means 5 can be employed in the probe 1 according to the present invention. For example, electrical or electromagnetic means are used to obtain a movement of the striking piston 2. In such an embodiment, the motor means comprise, for example, electromagnets or linear motors. In a variant embodiment, the striking piston 2 is driven by a hydraulic motor. The driving fluid is, for example, oil or water.

Advantageously, pneumatic motor means 5 are used. The striking piston 2 is driven by compressed air.

In a first variant embodiment, the probe 1 according to the present invent/on is independent and contains a source of energy. The probes 1 driven by electrical motor means contain storage batteries. In the case of pneumatic motor means 5, the probe contains a bottle of compressed air.

In a second variant embodiment, the probe 1 according to the present invention includes a cable 6 or a power supply tube. The cable 6 provides for furnishing to probe 1 the energy which it needs for operation, for example in the form of fluids under pressure and/or electrical current.

Advantageously, the tube or cable 6 is of small diameter, e.g., 30 mm. The cable 6 and/or the probe 1 could include a coating to reduce friction with the pulverulent material.

Advantageously, the cable 6 carries also control signals destined for a control device 7. The control device 7 makes it possible, for example, to change the direction of movement of the probe 1, to change over from forward movement to backward movement. The use of a remote control signal 8 to produce a change in direction of movement improves the reliability and the ease of use of the probe 1 of the present invention.

Advantageously, the probe 1 has means indicating its position within the mass of pulverulent material, a simple device for indicating its position, for example, in the case of a vertical movement consists of length graduations marked on the cable 6. To indicate any angular deviations, and in the case of autonomous probes, it may prove advantageous to use a position determining device 49. Device 49 contains, for example, a radio wave transmitter. Determination of the position of the probe I in the mass of pulverulent material will be made for example by triangulation using two or three directional receiving antennas.

Advantageously, the probe 1 according to the present invention has data acquisition means 43. The acquisition of data can be performed as a complement to a treatment to be performed on the pulverulent material, control the treatment in progress, or constitute the chief reason for the use of the probe 1 according to the present invention.

In a first variant embodiment, the data acquisition means 43 are coupled with recorders.

In a second variant embodiment, the data acquisition means are connected to the surface by a cable 6.

One particular variant of a data acquisition device consists in a device called a sampler. This device will be more particularly useful in taking samples of seeds at a predetermined depth, for example, inside of a silo, a pile or a ship's hold.

Advantageously, the probe 1 according to the present invention comprises a guiding tube 9. A guiding tube 9 placed in the axis of the probe 1 assures a rectilinear path of the probe. Moreover, the guiding tube prolongs the range of the probe in cases where its penetration of the pulverulent material would be limited. Thus, as shown in FIG. 1, the sample taking device 10 as well as another data acquisition device 43 are placed at the end of the guiding tube 9.

Advantageously, the probe 1 according to the present invention has guiding means.

In the example shown in FIG. 1, the probe 1 has excrescences 41 which can be deployed on the periphery of the probe.

In FIG. 1, the upper excrescence 41 is deployed and the lower excrescence 41 is retracted. In this case, under the action of the upper excrescence 41, the probe would have a tendency to veer toward the top of FIG. 1. Advantageously, the deployment and retraction of the excrescences 41 are remotely controlled. The remote-control signals are carried by cable 6, for example.

The probe 1 according to the present invention can be used for pushing or pulling solid devices to be deposited in the interior of a mass of pulverulent material.

For example, the probe 1 is pulling a filiform solid body 12, e.g., a ribbon, a cable, a line or a cord. In the example shown in FIG. 1, the body is intended to be abandoned. It is connected to a cap 11, for example, at the front end of the guiding tube 9. When the probe 1 is retracted, the cap will have nothing behind it, the body 12 will be left in the position determined by the end position of the guiding tube 9. It is well understood that connecting to some other point on the elements to being pulled or pushed—to the back of the probe for example—is not outside the scope of the invention.

Figure 2:
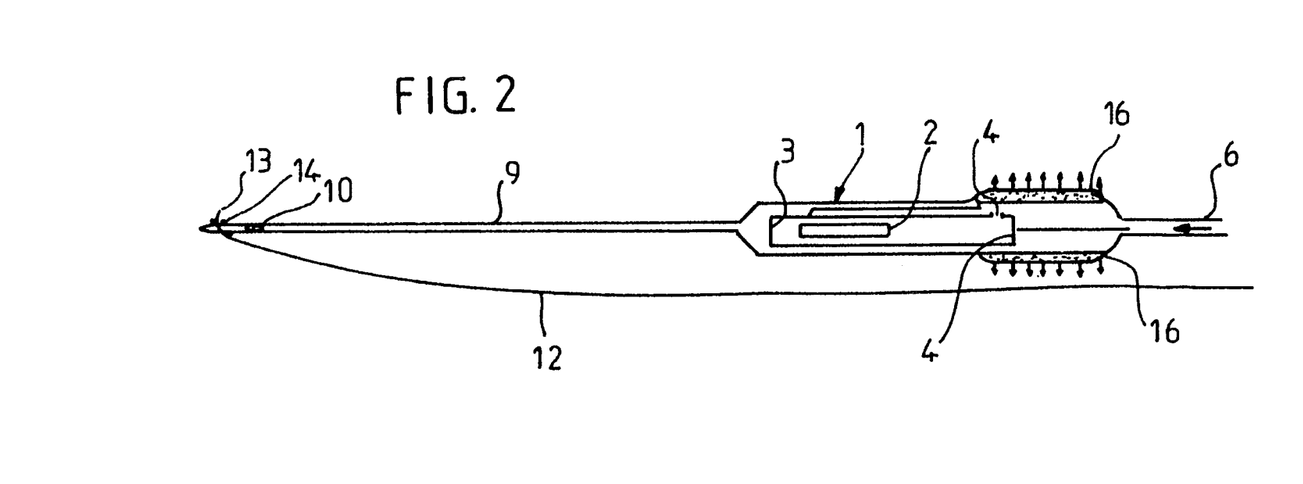
FIG. 2 is a sketch explaining a first example of the embodiment of a probe according to the present invention.

In FIG. 2 can be seen an embodiment of the probe 1 according to the present invention, with a pneumatic driver. The details of the known pneumatic motors are not represented in FIG. 2.

One originality of the probe 1 resides particularly in the fact that it includes means 16 permitting the escape of the compressed air into the mass of pulverulent material. For example, the probe 1 has ports 15 which put the air that has served to propel the striking piston 2 into communication with an exhaust surface 16 situated at the periphery of the probe 1. The radial exhaust is decidedly more effective than, for example, a rear exhaust. Furthermore, the radial exhaust permits the pulverulent material to be fluidized, which reduces the friction opposing the advance of the cable 6. The surface 16 comprises a filter preventing the penetration of the pulverulent material into the probe 1 while permitting the exhaust of the air to the exterior. The filter must be adapted to the pulverulent material or materials into which the probe 1 must penetrate. For grain, for example, a particularly high-performance filter made of sintered bronze has been used.

The direct exhaust of the air into the mass avoids having a conduit for the removal of the air to the exterior of the pulverulent material. Due to friction, such a conduit would increase resistance to the advance of the probe 1. Moreover, the air escaping from the pulverulent mass of material can have a beneficial effect on it. For example, the injection of dry air into the mass of grains contributes toward drying it and therefore to its preservation. It is even possible to increase the rate of flow of the exhaust air without advancing the probe, in order to improve drying.

The beneficent effect of the exhaust air can be increased by adding to it products for treatment. For example, products intended for the elimination of parasites from cereal grains can be added to the compressed air used for driving the probe. Thus an excellent diffusion is obtained for gaseous products, for example, such as methyl bromide or $PH_3$. Such products injected into a propelling gas are measured, for example, with a balance scale. The position of the probe 1 through which the injection or injections are made is determined with the aid of graduations present on the cable 6, and/or by using the means 49 for determining the position of the probe 1.

It is well understood that the exhausting of the air to the periphery of the probe is particularly effective with probes designed to penetrate into a pulverulent mass. However, it is well understood that the use of a radial exhaust with probes of the classical percussion type is no departure from the scope of the present invention.

In the example illustrated in FIG. 2, the forward end of the guide tube 9 has abutments or shoulders 14 staggered along its length. The staggered abutments 14 permit a ring 13 of large diameter to be hooked onto the guide tube. It is possible to hook onto the ring 13 a filiform body 12 which is to be deposited in the mass of the pulverulent material. Its large diameter allows for its reliable detachment when the probe I is withdrawn in reverse.

Figure 3:
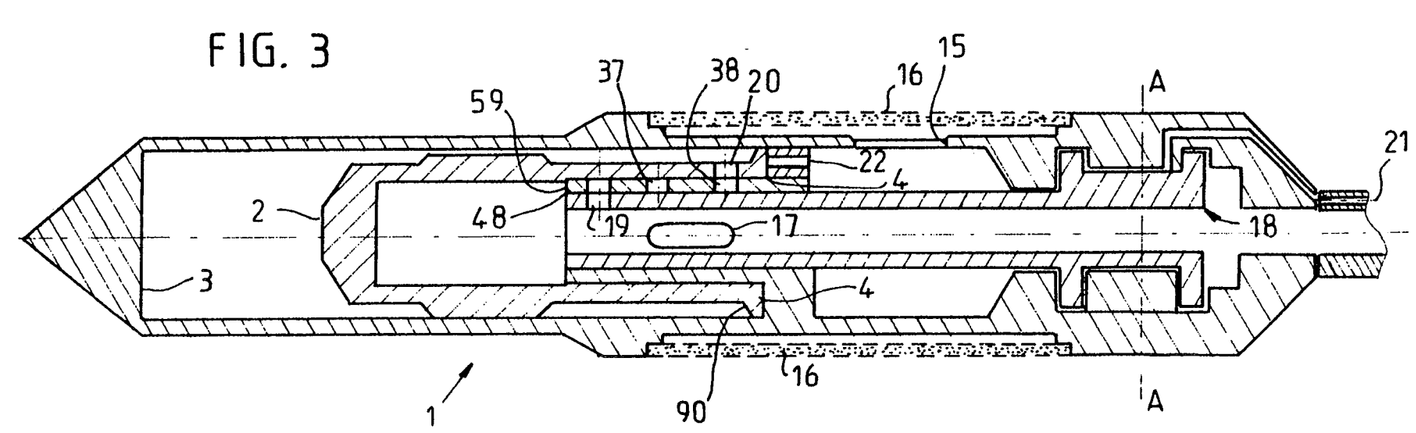
FIG. 3 is a sectional view of an example of embodiment of a probe according to the present invention in forward movement.
Figure 4:
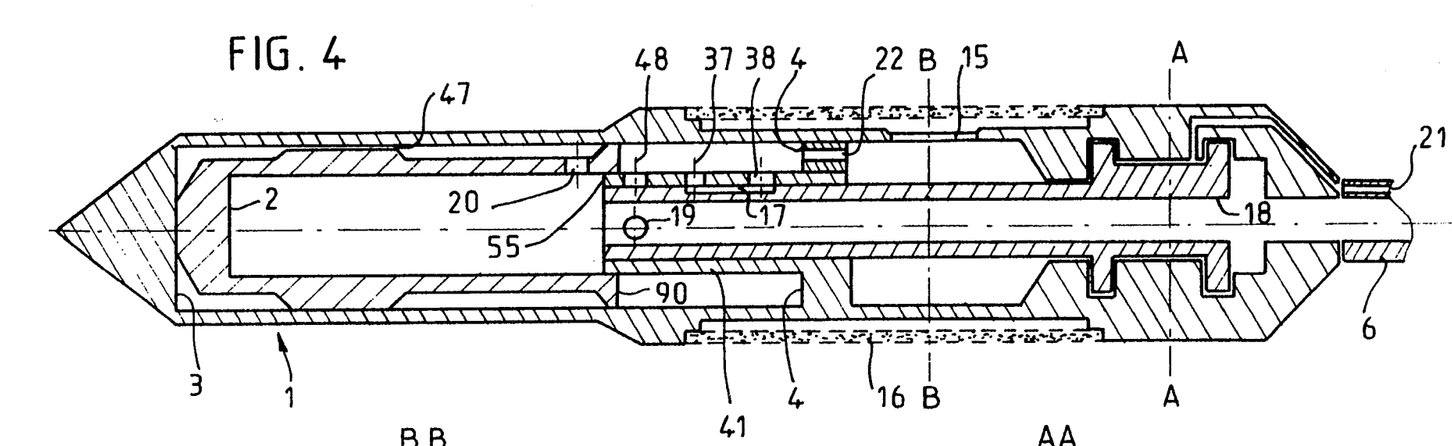
FIG. 4 is a sectional view of the probe of FIG. 3 in backward movement.

In FIGS. 3 and 4 can be seen an embodiment of a probe 1 according to the invention with a pneumatic drive.

In FIG. 3 the probe is in a state for retraction. The probe 1 of FIGS. 3 and 4 comprises a rigid hull covering also the zones 3 and 4. The hull can be disassembled for maintenance. However, the fact that the rigidity of the hull is assured, also at the level of the striking zones 3 and 4, permits good advancement into the pulverulent material.

The kinetic energy transmitted by the striking piston 2 to the forward striking zone 3 is distributed over the entire periphery of the hull of the probe 1. On the other hand, in variant embodiments, wherein the hull 1 according to the present invention (not illustrated) has a head connected by resilient means such as springs or pieces of rubber to the rest of the hull of the probe, 80% of the energy is concentrated at the head.

The use of a rigid probe avoids breaking the elements of pulverulent material into which it penetrates. It prevents, for example, breaking the grains of cereals. The fact of preventing the breaking of cereal grains is very important. On the one hand, the broken grains will be eliminated, for example before milling, by gauging operations. The mass of broken grains is lost. On the other hand, cargo containing broken grains is considered to be of poor quality and is therefore worth less than one containing no broken grains.

In the example of FIGS. 3 and 4, the striking piston 2 has a truncoconical front face integrated with a substantially cylindrical body. The front face strikes against the stroking zone 3 for forward operation, while the cylindrical portion strikes against a shoulder in the rear striking zone 4.

The striking piston 2 is not perfectly air-tight toward the front. It contains, for example, a groove 47 permitting the air to penetrate to its front face. On the other hand, the striking piston has at the back of its cylindrical portion a vent 20. At the back, the striking piston 2 has an air-tight ring 90.

The inside face of the cylindrical portion of the striking piston 2 slides along a sleeve 59 having three aligned cylindrical ports 48, 37 and 38. The rotary jack 18 has a cylindrical port 19 through its wall and an elongated slot 17. The port 19 and the slot 17 are placed at 90°. The port 19 is able to be put in communication the port 48. The slot 17 can put in communication with the ports 37 and 38.

The state illustrated in FIG. 3 corresponds to the rearward operation of the probe according to the present invention. The port 19 is placed in communication with the port 48. On the other hand, ports 37 and 38 are isolated, not being connected by the slot 17.

In FIG. 3, the striking piston 2 is shown in its rearmost position. The compressed air comes in via the conduit 6 and through the axis of the rotary jack 18. It pushes the striking piston 2 toward the striking zone 3. The port 20 of the striking piston 2 is connected through ports 48 and 19 to the compressed-air outlet. The compressed air escapes through a port not shown, and through the sintered bronze exhaust 16. Part of the air passes to the front face of the striking piston 2 through the groove 47. Its advancement has compressed the air that was ahead of its front face. Furthermore, the front face of the striking piston 2 has an area greater than that of the rear face. The compressed air that is in front of the front face of the striking piston causes the latter to recoil, and in recoiling covers again the ports 48 and 19 (which are no longer in communication with the ports 20) through which the exhaust is performed. The striking piston 2 yields its kinetic energy to the striking zone 4. The piston is back again in the position in which it is shown in FIG. 3, and the cycle begins again.

On a pneumatic command, the rotary jack 18 performs a quarter turn to the position shown in FIG. 4, corresponding to forward operation. In this case the port 19 no longer communicates with port 48. On the other hand, the slot 17 connects the ports 37 and 38. The compressed air coming from the conduit 6 passes through port 20 and groove 47. It thrusts the striking piston 2 toward the annular striking zone 4. The recoil of the striking piston 2 closes the port 20. Port 20 covers port 37 which permits the air to escape through: port 22, port 37, slot 17, and port 38, despite the presence of the ring 90. There is no more compressed air in front of piston 2. The striking piston 2 strikes the striking zone 3 under the action of the air arriving through conduit 6. Having lost its kinetic energy, it is pushed back by the compressed air. It is again the beginning of another cycle.

Figure 5:
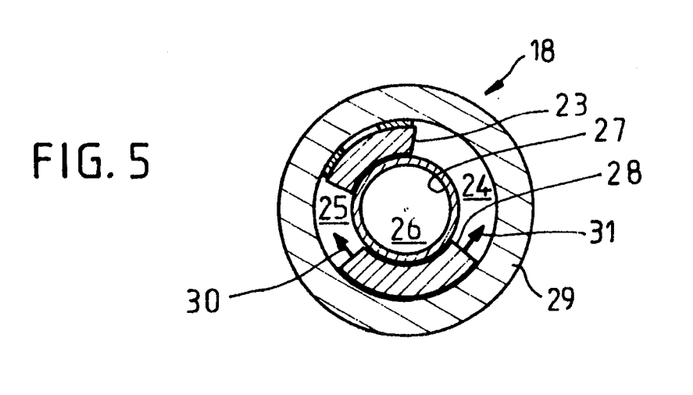
FIG. 5 is a sectional view of a rotary jack which can be embodied in a probe according to the present invention.

In FIG. 5 can be seen an embodiment of a rotary jack 18 which can be employed in the probe according to the present invention. The jack 18 comprises a body 29 to which is fastened a fixed block 23. A central air passage 26 is defined by a tube 27 as well as a movable block 28. The movable block 28 is attached to a piece of tubular shape (not shown in the figure) which can contain control ports. The rotary jack 18 can receive a control fluid, compressed air for example, in two chambers 24 and 25 created between the fixed block 23 and the movable block 28. By applying the control fluid to chamber 24 the movable block 28 is shifted in the direction of the arrow 30. By applying the control fluid to chamber 25, the movable block 28 is shifted in the direction of the arrow 31.

In a variant, the tubular part 27 and the movable block 28 are fastened together.

In the embodiment of FIG. 5, the movable block 28 can perform a rotation of three-quarters of a turn.

In a particularly advantageous variant, a revolving piece permits establishing the direction of movement of the probe. This revolving piece is driven by the rotation of a cable made, for example, of steel.

Figure 6A:
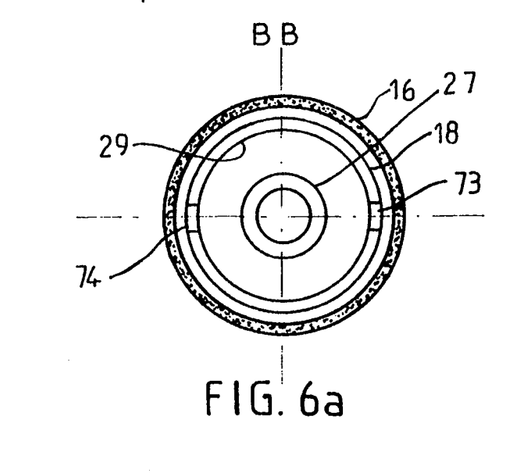
FIGS. 6a–6c are diagrams explaining the operation of the jack of FIG. 5.
Figure 6B:
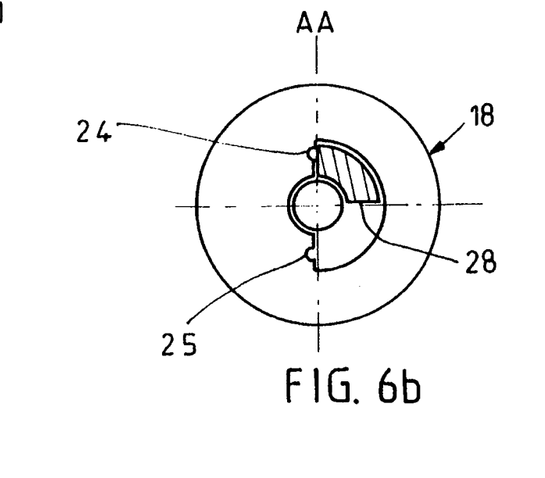
Figure 6C:
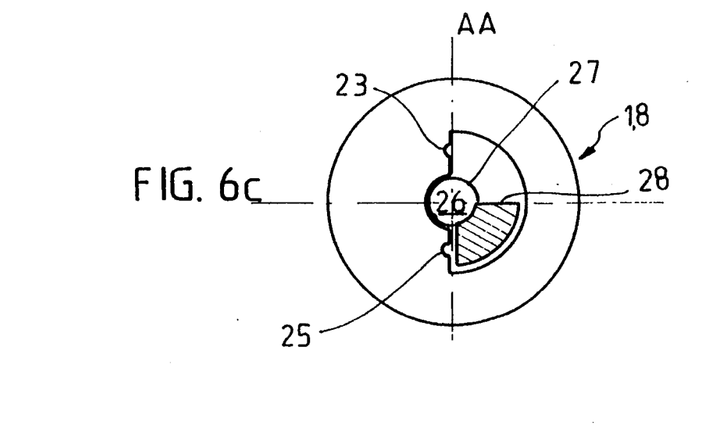

In FIG. 6, three cross sections through the probe 1 are represented. FIG. 6a corresponds to a cross section on line B—B of FIG. 4. FIG. 6b corresponds to cross section A—A through the probe of FIG. 4. FIG. 6c corresponds to cross section A—A through the probes of FIG. 3.

In the example of FIG. 6, the compressed-air control feed is provided by the grooves 24 and 25 of semicircular cross section. The movable block 28 is affixed to the tubular-shaped piece 27. The rotation of block 28 corresponds to 90°. In the example depicted in FIG. 6a, the exhaust passes through the ports 73 and 74. The use of a greater number of ports is not outside the scope of the present invention.

Figure 7:
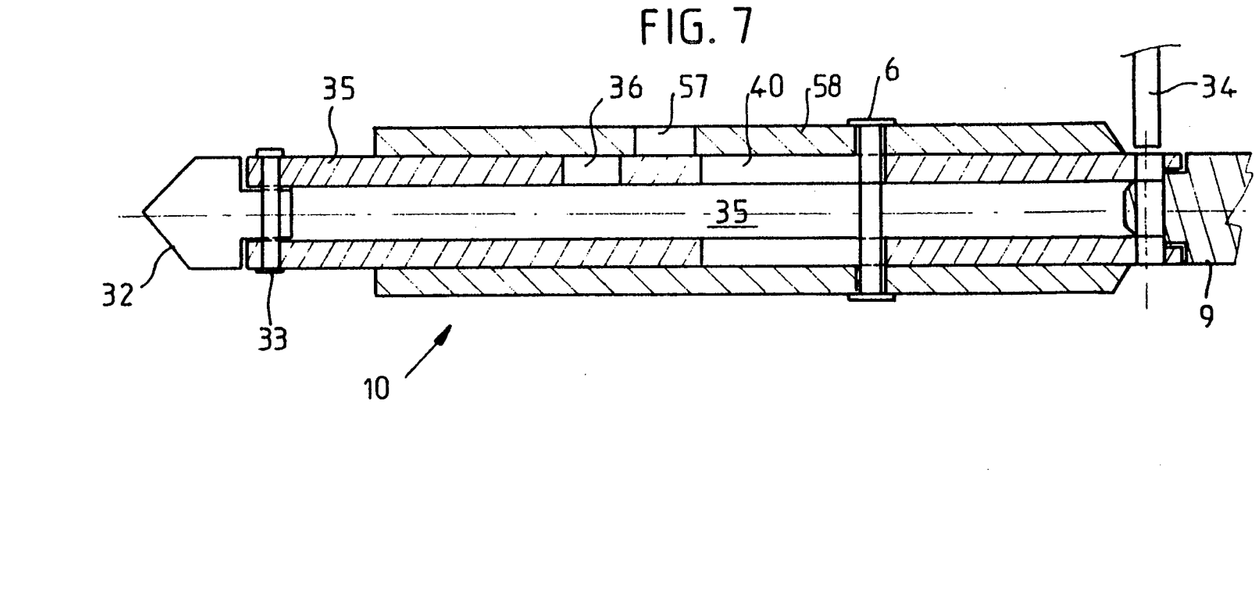
FIG. 7 is a sectional view of a sampling device which can be incorporated in the probe according to the invention.

In FIG. 7 can be seen an example of a sampling device 10. Advantageously, the device 10 for taking samples can be removably attached to the end of the guiding tube 9. In the example of FIG. 7, the attachment is made by a pin 34. The device 10 comprises an internal chamber 35 for receiving samples of pulverulent material. The chamber 35 is defined by the end of the tube 9, by a front plug 32, and by a tube 39. The plug 32 is attached by a pin 33. The originality of the device lies in the presence of the tube 58 which can slide coaxially on the tube 39. This sliding of tube 58 with respect to tube 39 is limited by a pin 41 passing through a slot 40 made in tube 39. Tube 39 has a port 36. A shaft 61 affixed to tube 58 passes through a port of elongated shape 40 made in the tube 39. The elongated port 40 defines the relative displacement of tubes 39 and 58. In one end position a port 36 of tube 39 is covered by the port 57 of tube 58. In this case the chamber 35 is communicated with the exterior, which causes filling with the pulverulent material, grain for example.

In a second embodiment of the device 10 according to the present invention, the port 40 of tube 39 is of sufficient length so that, in the end position, the port 36 of tube 39 is closed by the tube 58.

When the direction of movement is reversed, either when the desired depth has been reached, or due to an action intended solely for filling the chamber 35, tubes 39 and 58 slide one on the other as a result of friction exerted by the pulverulent material on the outer tube 58. At one moment, the two ports 57 and 36 are face to face and the filling of the chamber 35 takes place. The filling of chamber 35 ceases automatically when this chamber is full. The withdrawal of the probe in accordance with the present invention can therefore continue. In the second embodiment, the filling is performed only when port 57 passes in front of port 36. The withdrawal of the device 10 results in the closing of the port 36. The grain sampled at the point where it was taken is in no danger of being mixed with other grains surrounding the probe during its withdrawal.

In a first variant of the rotary jack 18 according to the present invention, the tube 27 provides for the air-tightness of the central passage 26 with respect to the chambers 24 and 25. In this variant, it is advantageous to provide the movable block 28 with substantially equal areas opening into each of the chambers 24 and 25.

In a second embodiment of the rotary jack according to the present invention, the chamber 24 or 25 corresponding to reverse operation is connected to the central passage 26. This saves the need for a tube to carry the backward control signal. Furthermore, in the absence of a remote control signal the probe is shifted to backward operation, which permits it to be recovered in case of malfunction. In the second variant of the jack 18, it may prove advantageous to provide the movable block 28 with unequal areas leading into the chambers 24 and 25. For example, an upper surface of the side of the chamber corresponding to forward movement permits performing the shift to forward movement with compressed air at the same pressure as that which serves to supply the motor means.

Figure 8:
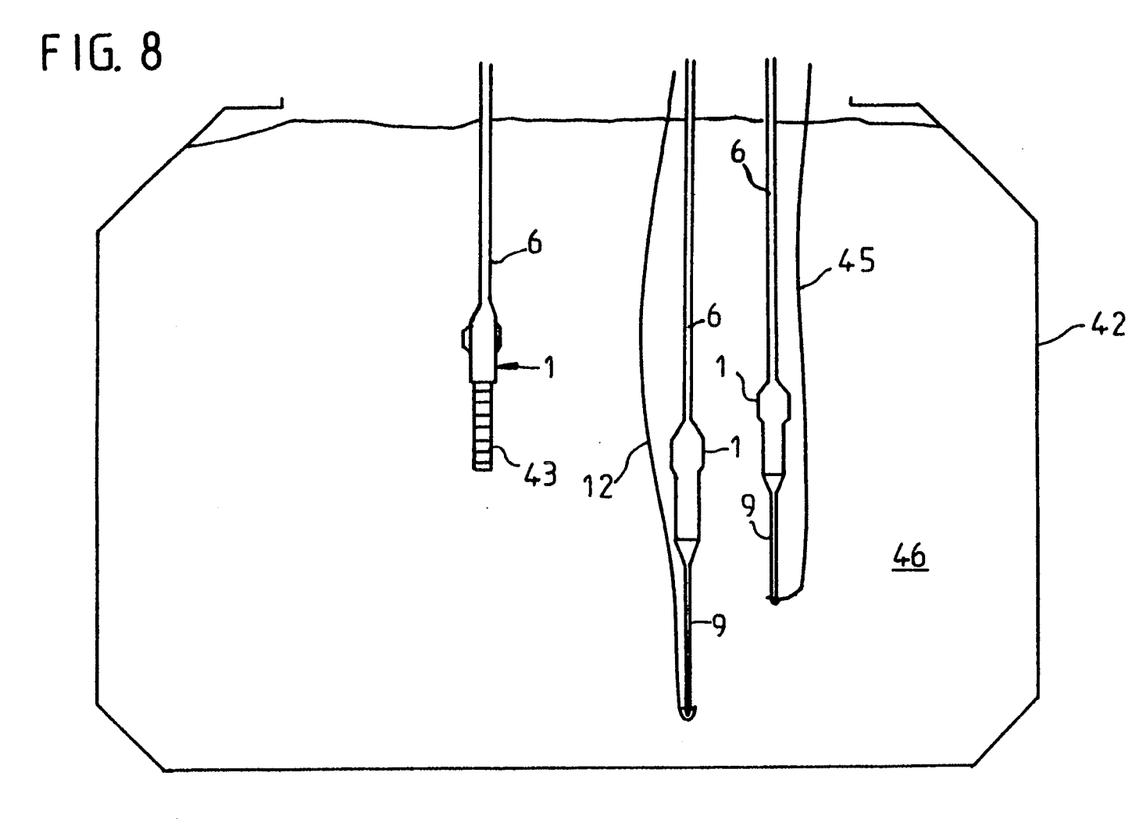
FIG. 8 illustrates the use of probes according to the present invention in the hold of a ship.

In FIG. 8 can be seen three examples of the use of a probe according to the present invention in the hold of a ship 42.

The probe 1 on the far left has a data acquisition device 43 intended to make sure that the grains stored in the hold 42 are of good quality and in good state of preservation. For example, a visual inspection is made, measurements are made of moisture content, pressure, temperature, or electrical resistivity, and/or the grains are sampled.

The center probe I carries out the permanent installation of a solid filiform body 12. This is, for example, a pipe or a sheath which is to be filled with tablets for a desired treatment, typically for the elimination of pests.

The probe 1 on the far right brings down a tube 45 to perform a spraying in the pulverulent material 46. This spray tube 45 is brought back up at the same time as the probe 1. It is, of course, possible to omit one or more of the operations mentioned above. It is possible, for example, to check the moisture content and then perform a drying of the grains or eliminate parasites only if their presence or the risk of their presence is detected.

Figure 9:
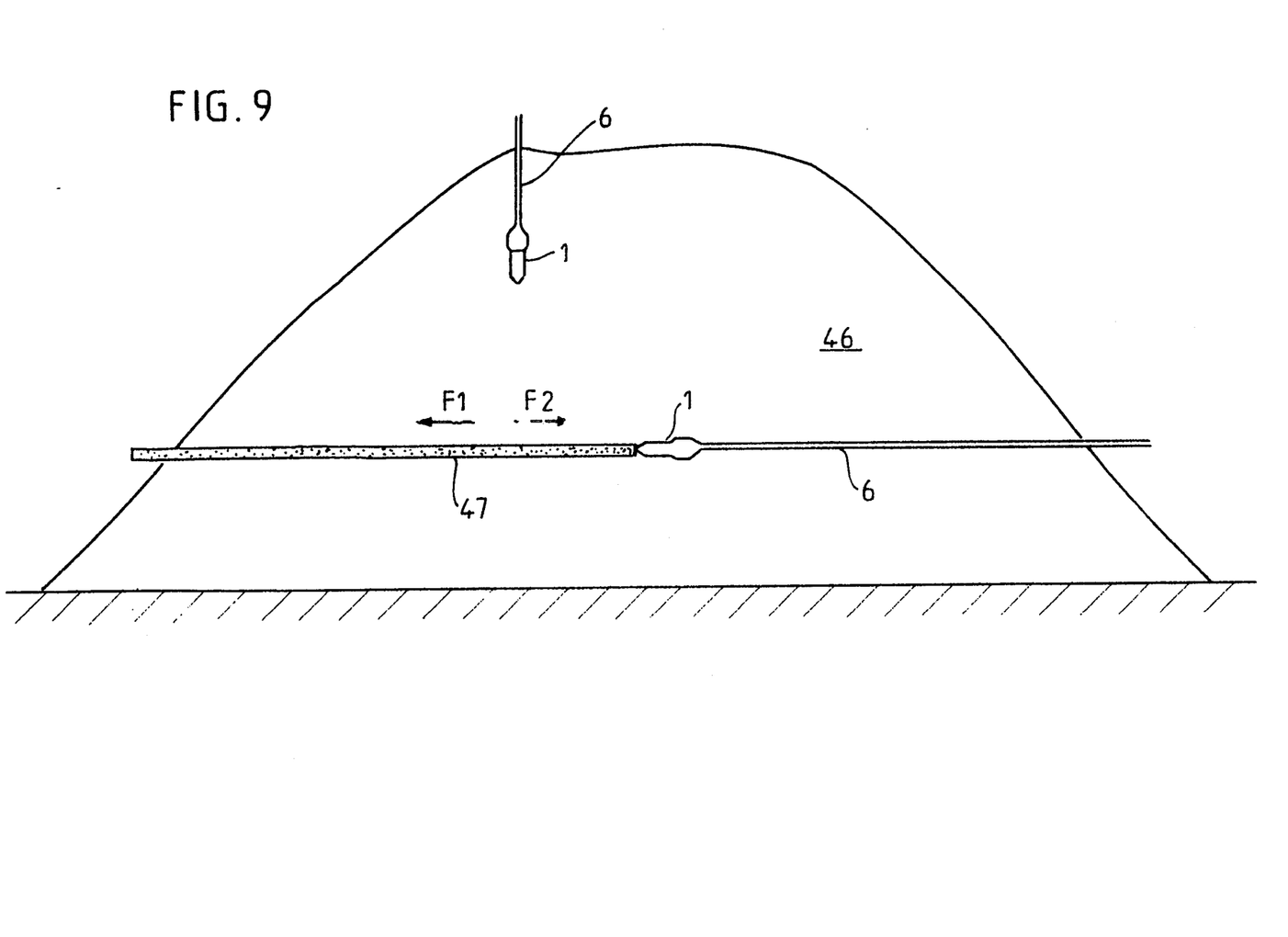
FIG. 9 illustrates the use of probes according to the present invention in a pile of pulverulent material.

In FIG. 9 can be seen an example of the use of the probe according to the present invention in a pile of pulverulent material 46. The pulverulent material 46 is grain, for example. In such a case it is possible to lower a probe 1 vertically in the same manner as the probes used in the hold 42 in FIG. 8. Furthermore, it is possible to make a probe penetrate horizontally, or even at a considerable angle. In the example of FIG. 9, the horizontal probe causes a tube 47 to penetrate into the pile of pulverulent material 46 for the purpose of aerating or treating it. Once the tubes have been deposited in the mass of pulverulent material, it is possible to perform the treatment (e.g., aeration, drying, injection of $CH_3Br$ or $PH_3$) even without having available a probe according to the present invention. In the embodiment, the probe 1 pushes the tube 47 in the direction of the arrow F1. In another embodiment, the probe 1 starts by advancing in the direction FI until it has passed through the pile of pulverulent material 46. Once it emerges on the other side, the tubes 47 are connected to it. It draws them into the pile of pulverulent material 46 as it is drawn back again in accordance with the arrow F2.

In a variant embodiment, not depicted, the probe according to the present invention pulls in front of it a tube whose inside diameter is greater than or equal to the diameter of the widest portion of the probe. The tube is pulled, for example, by means of a shoulder and a pin. Once the tube is in place the probe is withdrawn through the inside of the tube. Advantageously, a coupling prevents the entry of pulverulent material into the tube as it advances, while reducing, by its shape, resistance to its advancement.

The probe according to the present invention performs particularly well for the performance of treatments, and particularly sampling from a mass of farm products, particularly cereal grains stored in piles, in an elevator, or in the hold of a ship, at a depth of more than 3 meters. Indeed, for such depths, there does not exist any means permitting direct treatment, the taking of samples or inspection.

One variant of the method of the present invention consists in introducing a denaturing product permitting the marking of the mass of pulverulent material, particularly grains. Such marking makes it possible to distinguish, for example, grains intended for animal fodder. The denaturing product can be introduced either by using tubes disposed inside of the mass of pulverulent material, or, advantageously, by spraying the denaturing product into the air used in driving the probe.

The invention is applied chiefly to detection, to data acquisition, and to the laying of tubes in the pulverulent and/or heavy material, particularly agricultural products, and to the treatment of these materials.

The invention applies chiefly to the treatment of cereal grains.

I claim:

1. A probe assembly adapted to penetrate a pulverulent mass of food grains, such probe assembly comprising a hull defining a cylindrical hollow therein, a striking zone integral with the hull and located in the hollow at one end thereof, a striking piston disposed within the hollow and slidable between a first position remote from said striking zone and a second position impacting against said striking zone, and a pneumatic motor actuatable by compressed air for projecting said striking piston against said striking zone, said striking piston being adapted to transmit to the hull substantially all the kinetic energy of the striking piston, thereby moving the probe assembly by itself within the mass of food grains, exhaust means located on the sides of the hull for exhausting the air from the pneumatic motor after each impact of the striking piston on a striking zone, wherein said exhaust means includes an external filter to prevent any entry of food grains into the interior of the hull.

2. A probe assembly according to claim 1, wherein said external filter is sintered bronze.

3. A probe assembly according to claim 1, further including remote control means for selecting the direction of projection of the striking piston, wherein said remote control means comprises a cable.

4. A probe assembly according to claim 1, further comprising a guiding tube of elongated shape rigidly connected to the front of the hull.

5. A probe assembly according to claim 1, further including retractable excrescences on its sides and remote guiding means associated therewith for controlling the excrescences 6. A probe assembly according to claim 1, further including sampling means for obtaining small specimens of the mass of food grains.

7. A probe assembly according to claim 1, further including connecting means secured to the hull for pushing or pulling tubes within the mass of food grains.

* * * * *